United States Patent [19]
Townson et al.

[11] Patent Number: 5,888,934
[45] Date of Patent: Mar. 30, 1999

[54] HERBICIDAL COMPOSITIONS AND ADJUVANT COMPOSITION COMPRISING ALKYLPOLYGLYCOSIDE AND ETHOXYLATED ALCOHOL SURFACTANTS

[75] Inventors: Jane Karen Townson, Maidenhead; Clifford Arthur Hart; Martin Keith Osborn, both of Wokingham; Michael John Bean, Bracknell, all of United Kingdom

[73] Assignee: Zeneca Limited, United Kingdom

[21] Appl. No.: 750,168

[22] PCT Filed: Jun. 7, 1995

[86] PCT No.: PCT/GB95/01310

§ 371 Date: Nov. 19, 1996

§ 102(e) Date: Nov. 19, 1996

[87] PCT Pub. No.: WO96/00010

PCT Pub. Date: Jan. 4, 1996

[30] Foreign Application Priority Data

Jun. 24, 1994 [GB] United Kingdom .................... 9412722

[51] Int. Cl.$^6$ ............................. A01N 25/30; A01N 57/02
[52] U.S. Cl. ............................................................. 504/206
[58] Field of Search ...................... 504/116, 206; 252/351

[56] References Cited

U.S. PATENT DOCUMENTS

| | | | |
|---|---|---|---|
| 5,317,003 | 5/1994 | Kassebaum et al. | 504/116 |
| 5,658,853 | 8/1997 | Kassebaum et al. | 504/206 |

FOREIGN PATENT DOCUMENTS

| | | |
|---|---|---|
| 0 256 608 | 2/1988 | European Pat. Off. . |
| 0 257 686 | 3/1988 | European Pat. Off. . |
| 0 364 202 | 4/1990 | European Pat. Off. . |
| 0 498 145 | 8/1992 | European Pat. Off. . |
| 0 498 785 | 8/1992 | European Pat. Off. . |
| 0 526 443 | 2/1993 | European Pat. Off. . |
| 0 531 269 | 3/1993 | European Pat. Off. . |
| 2 589 328 | 5/1987 | France . |
| 39 25 846 | 2/1991 | Germany . |
| WO91 00010 | 1/1991 | WIPO . |
| WO92 01508 | 2/1992 | WIPO . |
| WO94 02021 | 2/1994 | WIPO . |
| WO95 02327 | 1/1995 | WIPO . |
| WO95 03881 | 2/1995 | WIPO . |
| WO95 16351 | 6/1995 | WIPO . |

OTHER PUBLICATIONS

Sherrick et al., *Weed Science*, Nov. 1986, Issue 6, V. 34:817–823, "Absorption and Translocation of MON 0818 Adjuvant in Field Bindweed (*Convolvulvus arvensis*)".

Green & Green, *Weed Technology*, Jul.–Sep. 1993, V. 7:633–640, "Surfactant Structure and Concentration Strongly Affect Rimsulfuron Activity".

Smith et al., *Wed Res.*, 1966, V. 6:233–242, "Structure–Activity Relationships of Alkyl–phenol Ethylene Oxide Ether Non–Ionic Surfactants and Three Water–Soluble Herbicides".

Knoche & Bukovac, *Weed Science*, Jan.–Mar. 1993, Issue 1, V. 41:87–93, "Interaction of Surfactant and Leaf Surface in Glyphosate Absorption".

Gaskin & Holloway, *Pesticide Science*, 1992, V. 34:195–206, "Some Physicochemical Factors Influencing Foliar Uptake Enhancement of Glyphosatemono (isopropy-l–ammonium) by Polyoxyethylene Surfactants".

*Primary Examiner*—S. Mark Clardy
*Attorney, Agent, or Firm*—Marian T. Thomson; David P. LeCroy

[57] ABSTRACT

A glyphosate composition comprises (I) N-phosphonomethylglycine or an agriculturally acceptable salt thereof, (ii) an alkyl polyglycoside surfactant, (iii) an ethoxylated alcohol, for example an ethoxylated alcohol obtained by ethoxylation of a linear or branched chain aliphatic mono alcohol having a chain length of from 8 to 20 carbon atoms and a mean degree of ethoxylation of from 2 to 50 moles of ethylene oxide per mole of alcohol, and optionally (iv) an additional surfactant, and optionally (v) a humectant.

14 Claims, No Drawings

HERBICIDAL COMPOSITIONS AND ADJUVANT COMPOSITION COMPRISING ALKYLPOLYGLYCOSIDE AND ETHOXYLATED ALCOHOL SURFACTANTS

This invention relates to a herbicidal composition and in particular to a glyphosate composition.

The term "glyphosate composition" is used herein to mean a herbicidal composition comprising as active ingredient N-phosphonomethylglycine or a herbicidally acceptable salt thereof.

Herbicidally active glyphosate compositions are well known and are commercially available in the form of the trimethylsulphonium, isopropylamine and other salts. Such compositions are generally applied to unwanted vegetation in the form of an aqueous formulation containing a variety of adjuvants including for example wetters or other surface-active agents, anti-freeze agents, dyes, dispersants, Theological agents, anti-foam agents and humectants. The activity of the glyphosate composition may be improved considerably by the careful choice of additives. The literature contains many hundreds of examples of different glyphosate formulations exhibiting a variety of properties and designed for a variety of purposes.

In EP 0531269 for example there is disclosed a herbicidal composition comprising glyphosate or an agriculturally acceptable salt thereof and an acetylenic diol surfactant structurally characterized by a symmetrically substitued triple bond and adjacent hydroxyl groups or adjacent polymeric oxalkylated units, and optionally a second surfactant.

In EP 0526443 there is disclosed a compostion comprising a glyphosate herbicide, and activity ehnhancing alkylpolyglycoside and a foam moderating acetylenic diol.

Glyphosate compositions are very effective in killing unwanted weeds to which they are applied. However the uptake of the glyphosate composition by the plant leaf surface is relatively slow. In consequence the composition may be washed off the leaf surface and the herbicidal effectiveness may be reduced or even lost if rain falls shortly after application of the composition (for example within 6 hours of application). This is a particular problem for example in tropical climates in which it is difficult to predict the occurrence of heavy rain showers. Glyphosate compositions have been produced which are.claimed to give improved rainfastness, but the topic is poorly understood and the physical parameters involved are highly complex and may vary from species to species. It may for example be appropriate to provide a composition which generally improves rainfastness for most species but is relatively ineffective on particular individual species. One approach which has been studied is to seek to improve the rate of uptake of the glyphosate composition into the leaf surface with a view to minimising the susceptibility to rain. Such improved uptake is often only achieved however at the expense of localised tissue damage and reduced translocation. It is clearly important that improved rainfastness is not associated with a significant reduction in herbicidal activity in the absence of rain. It is therefore desired to provide a glyphosate composition combining good activity in the absence of rain with effective rainfastness.

The present invention seeks to provide herbicidally effective compositions having improved rainfastness, by which is meant that compositions of the present invention generally reduce the overall loss in herbicidal effectiveness resulting from a fall of rain within for example from 1 to 6 hours after application of the composition. Compositions of the present invention may also show enhanced activity as compared with known glyphosate compositions and advantage as compared with known compositions may be found in either one or in both of these effects.

According to the present invention there is provided a glyphosate composition comprising (i) N-phosphonomethylglycine or an agriculturally acceptable salt thereof, (ii) a alkylpolyglycoside surfactant and (iii) an ethoxylated alcohol wherein the ethoxylated alcohol is obtained by ethoxylation of a linear or branched chain aliphatic mono alcohol having a chain length of from 8 to 20 carbon atoms and has a mean degree of ethoxylation of from 2 to 50 moles of ethylene oxide per mole of alcohol.

The alkylpolyglycoside for use in the present invention may be obtained by the reaction of alkanols with glucose or other mono- or di- or polysaccharides. As used herein the term "alkylpolyglycoside" includes an alkylmonoglycoside. Preferred alkylpolyglycosides for use in the present invention are alkylpolyglucosides obtained by the reaction of glucose with a straight or branched chain alkanol or mixture of alkanols, for example a mixture of alkanols containing 7 to 18, preferably 7 to 16 carbon atoms for example 8 to 10 carbon atoms. The number of glycose groups per alkyl group in the molecule may vary and alkyl mono- or di- or polyglucose or saccharide derivatives are possible. Commercial alkylpolyglucosides usually contain a mixture of derivatives having an average number of glycose groups per alkyl group (degree of polymerisation) of between 1 and 4, for example from about 1 to 2. A number of suitable alkylpolyglycosides are commercially available and include for example AL2042 (ICI); AGRIMUL 2069 (Henkel) and ATPLUS 258 (ICI). Saccharide-based surfactants which may be used include derivatives of mono-, di- or polysaccharides, including for example fatty acid esters of mono-, di- or polysaccharides. Such surfactants are commercially available for example under the trade mark CRODESTA (Croda).

The ethoxylated alcohol is preferably obtained by ethoxylation of a linear or branched chain aliphatic mono alcohol or a mixture of such alcohols having an average chain length of from 10 to 18 carbon atoms. An example of an ethoxylated alcohol for use in the present invention is that derived from a mixture of an alcohol containing 13 carbon atoms and an alcohol containing 15 carbon atoms. The ratio of the C13 alcohol to the CI alcohol is typically from 30:70 to 70:30 and the mixture generally contains both linear and branched alchols, for example about 50% by weight of linear alcohols. An example of an ethoxylated aromatic alcohol is nonylphenol ethoxylate.

The mean degree of ethoxylation (mean molar ethylene oxide content) is preferably from 10 to 20 moles of ethylene oxide per mole of alcohol. The most efficacious degree of ethoxylation may vary somewhat depending upon the weed species being treated. It is therefore possible either to select the most efficacious mean degree of ethoxylation for a specific target weed or to seek an mean degree of ethoxylation which is efficacious over a broad range of species. In general we have found that effective treatment over a broad range of species is obtained when the mean degree of ethoxylation is from 11 to 18 moles of ethylene oxide per mole of alcohol. There may in some instances be an advantage in obtaining a broad species response by using a composition having a broad distribution of ethylene oxide content around the mean value. The appropriate mean ethylene oxide content may if desired be obtained by mixing two or more commercially available ethoxylated alcohols having various ethylene oxide contents in the appropriate ratio. This has the dual advantage of enabling a desired mean ethylene oxide content to be achieved precisely and also of ensuring that a broad distribution of ethylene oxide contents is present. Thus for example a mean ethylene oxide content of about 15 moles of ethylene oxide per mole of alcohol may be achieved by mixing the commercially available ethoxylated alcohol SYNPERONIC A11 (SYNPERONIC IS A TRADEMARK OF IMPERIAL CHEMICAL INDUSTRIES PLC) which has a mean ethylene oxide content of 11 with SYNPERONIC A20 (which has a mean ethylene oxide content of 20) in the ratio 3 to 2.

A number of suitable ethoxylated alcohols are commercially available including for example the SYNPERONIC A series having a range of ethylene oxide contents (indicated by the number after the "A") and based on a $C_{13}$–$C_{15}$ alcohol containing about 50% by weight linear alcohol, the remainder being mainly mono-brached; CIRRASOL ALN-WF (a mixture of C16–C18 linear alcohols with a mean ethylene oxide content of 17); BRIJ 96 and 98 based on an unsaturated $C_{18}$ linear alcohol and having a mean ethylene oxide content of 10 and 20 respectively; and RENEX 30 based on a branched $C_{13}$ alcohol having a mean ethylene oxide content of 12.

The N-phosphonomethylglycine or agriculturally acceptable salt thereof is conveniently the trimethylsulphonium, isopropylamine, sodium, or ammonium salt, although N-phosphonomethylglycine itself or any agriculturally acceptable salt thereof is acceptable for incorporation in the composition of the present invention. It is preferred to use a water-soluble salt of N-phosphonomethylglycine.

The composition of the present invention may be a dilute aqueous herbicidal composition which is sold ready for immediate use or may be formulated as an aqueous herbicidal concentrate which is diluted prior to use. Alternatively, the components of the composition may be mixed together and diluted shortly before application.

Thus in one embodiment of the present invention there is provided an aqueous herbicidal concentrate which is sufficiently storage-stable for commercial use and which is diluted before use, usually with water. The term "herbicidal concentrate" covers a range of compositions from the relatively dilute which requires the addition of relatively little water to a more concentrated composition which has a high content of glyphosate and thus has advantages for handling and transportation. The preference for a concentrated glyphosate rainfast composition poses an additional problem which must be solved, since many adjuvants are incompatible with each other or with the active ingredient in concentrated compositions. By the term "concentrated" glyphosate composition is meant a composition having a concentration greater than 210 g/l for example greater than 220 g/l based on glyphosate acid. In the case for the trimethylsulphonium salt of glyphosate for example, this equates to a concentration of greater 304 g/l and more particularly greater than about 319 g/l based on the salt.

In an alternative embodiment of the present invention the alkyl polyglycoside and the ethoxylated alcohol may be formulated together, optionally with other adjuvants such as an inorganic salt or one or more additional surfactants as described below, to form an adjuvant composition suitable for tank mixing with a glyphosate composition. The adjuvant composition is tank mixed prior to use, for example with a commercially available glyphosate composition. The glyphosate composition could be an aqueous formulation containing essentially only glyphosate or could itself contain suitable adjuvants.

Thus according to a further aspect of the present invention there is provided an adjuvant composition suitable for admixture with N-phosphonomethylglycine or an agriculturally acceptable salt thereof to form a composition according to the present invention, which adjuvant composition comprises (i) a alkylpolyglycoside surfactant and (ii) an ethoxylated alcohol wherein the ethoxylated alcohol is obtained by ethoxylation of a linear or branched chain aliphatic mono alcohol having a chain length of from 8 to 20 carbon atoms and has a mean degree of ethoxylation of from 2 to 50 moles of ethylene oxide per mole of alcohol and optionally (iii) an additional surfactant.

The proportion of alkylpolyglycoside present in the herbicidal composition or in the adjuvant composition is preferably from 1 part by weight alkylpolyglycoside per 5 parts by weight ethoxylated alcohol to 8 parts by weight alkylpolyglycoside per 1 part by weight ethoxylated alcohol and most preferably from 0.5 parts by weight alkylpolyglycoside per 1 part by weight ethoxylated alcohol to 8 parts by weight alkylpolyglycoside per 1 by weight part ethoxylated alcohol for example from 1 part by weight alkylpolyglycoside per 1 part by weight ethoxylated alcohol to 8 parts by weight alkylpolyglycoside per 1 by weight part ethoxylated alcohol. An especially preferred composition contains about equal proportions by weight of alkylpolyglycoside and ethoxylated alcohol.

If the composition contains a relatively high proportion of ethoxylated alcohol it may be desirable to add an additional surfactant to enhance stability, especially if the composition is used in the form of an aqueous concentrate. A wide range of suitable additional surfactants will occur to those skilled in the art and those which have been found to enhance stability include cationic or nonionic surfactants containing an amine, ammonium or amine oxide group for example quaternary tetra-alkyl ammonium salt surfactants such as hexadecyl trimethyl ammonium chloride; and primary, secondary or quaternary optionally ethoxylated long-chain alkyl amines such as coco-amine or hydrogenated tallow amine each having a mean ethylene oxide content of from 2 to 20 when ethoxylated. In some instances, the additional surfactant may even provide an increase in the activity of the composition. Thus especially preferred additional surfactants are optionally ethoxylated quaternary ammonium salts having at least one long chain substituent containing from 10 to 20 carbon atoms and mean ethylene oxide content of from 0 to 5. Examples of suitable additional surfactants include hexadecyl trimethyl ammonium chloride, trimethyl tallowammonium chloride, trimethyl cocoammonium chloride and N-methyl cocoammonium chloride having a mean ethylene oxide content of 2. It has been found that the presence of a mean ethylene oxide content of from about 1 to 5, for example about 2 provides an enhanced low-temperature stability for the formulation.

Thus according to a still further aspect of the present invention there is provided an adjuvant composition suitable for admixture with N-phosphonomethylglycine or an agriculturally acceptable salt thereof, which composition comprises (i) a alkylpolyglycoside surfactant (ii) an ethoxylated alcohol wherein the ethoxylated alcohol is obtained by ethoxylation of a linear or branched chain aliphatic mono alcohol having a chain length of from 8 to 20 carbon atoms and has a mean degree of ethoxylation of from 2 to 50 moles of ethylene oxide per mole of alcohol and (iii) an optionally ethoxylated quaternary ammonium salt having at least one long-chain substituent containing from 10 to 20 carbon atoms and a mean ethylene oxide content of from 0 to 5.

The proportion of additional surfactant is preferably from 0 to 2 parts by weight per 1 part by weight of ethoxylated alcohol and more preferably about 1 part by weight per 1 part by weight of ethoxylated alcohol. Thus an especially preferred composition comprises a total adjuvant system comprising substantially equal proportions by weight of alkylpolyglycoside, ethoxylated alcohol and additional surfactant.

Compositions containing glyphosate, alkylpolyglycoside, ethoxylated alcohol and preferred additional surfactants have been found to classified as having only low skin and eye irritancy, and this provides a further commercial advantage.

The proportion by weight of the total adjuvant system (alkylpolyglycoside, ethoxylated alcohol and any additional surfactant used) to the glyphosate salt in a concentrate composition is preferably from 3:1 to 1:3 and especially from 1:1 to 1:3. A ratio of about 1:2 is especially preferred. Higher proportions of adjuvant system may be used if desired in a tank mix or ready to use composition.

We have found that the activity of the present composition may generally be enhanced by the incorporation of a humectant.

Thus according to a further aspect of the present invention there is provided a glyphosate composition comprising (i) N-phosphonomethylglycine or an agriculturally acceptable salt thereof, (ii) a alkylpolyglycoside surfactant wherein the ethoxylated alcohol is obtained by ethoxylation of a linear or branched chain aliphatic mono alcohol having a chain length of from 8 to 20 carbon atoms and has a mean degree of ethoxylation of from 2 to 50 moles of ethylene oxide per mole of alcohol, (iii) an ethoxylated linear or branched chain alcohol and (iv) a humectant.

Suitable humectants include glycerol, polyethylene glycol, sorbitol, ethylene glycol, propylene glycol and lactate salts such as sodium or ammonium lactate. For the compositions of the present invention we have found that glycerol, polyethylene glycol, sorbitol and sodium lactate are especially effective in enhancing activity. When polyethylene glycol is used as humectant, the molecular weight is preferably in the range 100 to 1200 and more particularly from 200 to 1000. The enhancement of activity provided by polyethylene glycol of a given molecular weight depends to some extent on the target weed species, but in general a low-molecular weight especially preferred. Higher proportions of adjuvant system may be used if desired in a tank mix or ready to use composition.

We have found that the activity of the present composition may generally be enhanced by the incorporation of a humectant.

Thus according to a further aspect of the present invention there is provided a glyphosate composition comprising (i) N-phosphonomethylglycine or an agriculturally acceptable salt thereof, (ii) a alkylpolyglycoside surfactant, (iii) an ethoxylated linear or branched chain alcohol and (iv) a humectant.

Suitable humectants include glycerol, polyethylene glycol, sorbitol, ethylene glycol, propylene glycol and lactate salts such as sodium or ammonium lactate. For the compositions of the present invention we have found that glycerol, polyethylene glycol, sorbitol and sodium lactate are especially effective in enhancing activity. When polyethylene glycol is used as humectant, the molecular weight is preferably in the range 100 to 1200 and more particularly from 200 to 1000. The enhancement of activity provided by polyethylene glycol of a given molecular weight depends to some extent on the target weed species, but in general a low-molecular weight polyethylene glycol, for example a polyethylene glycol of molecular weight about 200, is preferred.

The humectant is most conveniently used in a tank mix composition or in a ready to use composition. The proportion is preferably from 1 part of glyphosate salt per 1 part humectant to 1 part glyphosate salt per 20 parts humectant.

The composition of the present invention may additionally include an inorganic ammonium salt such as ammonium sulphate as an activity-enhancing adjuvant. The proportion of ammonium sulphate (if used) is preferably from 1 part inorganic ammonium salt per 1 part glyphosate salt to 10 parts ammonium salt per 1 part glyphosate salt. The ammonium salt is most conveniently used in a tank mix composition or in a ready to use composition.

Compositions of the present invention are active against a broad range of weed species including monocotyledonous and dicotyledonous species. The compositions of the present invention are suitably applied directly to unwanted plants (post-emergence application). Particularly important species which should be effectively controlled if a formulation is to polyethylene glycol, for example a polyethylene glycol of molecular weight about 200, is preferred.

The humectant is most conveniently used in a tank mix composition or in a ready to use composition. The proportion is preferably from 1 part of glyphosate salt per 1 part humectant to 1 part glyphosate salt per 20 parts humectant.

The composition of the present invention may additionally include an inorganic ammonium salt such as ammonium sulphate as an activity-enhancing adjuvant. The proportion of ammonium sulphate (if used) is preferably from 1 part inorganic ammonium salt per 1 part glyphosate salt to 10 parts ammonium salt per 1 part glyphosate salt. The ammonium salt is most conveniently used in a tank mix composition or in a ready to use composition.

Compositions of the present invention are active against a broad range of weed species including monocotyledonous and dicotyledonous species. The compositions of the present invention are suitably applied directly to unwanted plants (post-emergence application). Particularly important species which should be effectively controlled if a formulation is to achieve commercial success are Elymus-repens and Sorghum halepense. We have found that compositions of the present invention are particularly effective against these species.

Thus according to a further aspect of the present invention there is provided a process of severely damaging or killing unwanted plants, and more particularly a process of providing enhanced activity or enhanced rainfastness which comprises applying to the plants a herbicidally effective amount of a composition of the present invention.

Compositions of the present invention include both solid compositions, dilute compositions, which are ready for immediate use, and concentrated compositions, which require to be diluted before use, usually with water. Preferably the compositions contain from 0.01% to 90% by weight of the agriculturally acceptable salt of N-phosphonomethylglycine. Dilute compositions ready for use preferably contain from 0.01 to 2% of agriculturally acceptable salt of N-phosphonomethylglycine, while concentrated compositions may contain from 20 to 90% of agriculturally acceptable salt of N-phosphonomethylglycine, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution, suspension or dispersion of the active ingredients in water optionally containing a surface-active agent, or may comprise a solution or dispersion of the active ingredient in a water-immiscible organic solvent which is dispersed as droplets in water. Preferred active ingredients of the composition of the present invention are water-soluble herbicides or are readily suspended in water and it is preferred to use aqueous compositions and concentrates. In particular, the trimethylsulphonium, isopropylamine, sodium and ammonium salts of glyphosate are all readily soluble in water.

The composition of the present invention may contain additional surface active agents, including for example surface active agents to increase the compatibility or stability of concentrated compositions as discussed above. Such surface-active agents may be of the cationic, anionic, non-ionic or amphoteric type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl- phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble or dispersible surface active agents having a skeleton which comprises a siloxane chain e.g. Silwet L77). A suitable mixture in mineral oil is ATPLUS 411F.

The aqueous solutions or dispersions may be prepared by dissolving the active ingredients in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene, although as indicated above it is preferred to use an entirely aqueous system for compositions of the present invention.

The compositions for use in the form of aqueous solutions or dispersions are generally supplied in the form of a concentrate containing a high proportion of the active ingredients, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–70%, preferably 20–50%, by weight of the agriculturally acceptable salt of N-phosphonomethylglycine. Dilute preparations ready for use may contain varying amounts of the agriculturally acceptable salt of N-phosphonomethylglycine depending upon the intended purpose; amounts of 0.01% to 10.0% and preferably 0.1% to 2%, by weight of agriculturally acceptable salt of N-phosphonomethylglycine are normally used.

Other additives and adjuvants may also be present in compositions of the present invention. Examples include anti-freeze agents such as ethylene glycol and propylene glycol; dyes; dispersants; rheological agents; and anti-foam agents such as silicone based agents.

The rate of application of the composition of the invention will depend on a number of factors including, for example, the active ingredients chosen for use, the identity of the plants whose growth is to be inhibited and the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may also comprise one or more additional compounds which possess biological activity, for example herbicides, fungicides, insecticides (optionally with an insecticide synergist) and plant growth regulators.

The other herbicide may be any herbicide other than a glyphosate salt. It will generally be a herbicide having a complementary action in the particular application.

Examples of useful complementary herbicides include:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);

C. 1,3 dimethylpyrazole derivatives such as pyrazoxyfen, pyrazolate and benzofenap;

D. Dinitrophenols and their derivatives (eg. acetates) such as dinoterb, dinoseb and its ester, dinoseb acetate;

E. dinitroaniline herbicides such as dinitramine, trifluralin, ethalflurolin, pendimethalin, oryzalin;

F. arylurea herbicides such as diuron, flumeturon, metoxuron, neburon, isoproturon, chlorotoluron, chloroxuron, linuron, monolinuron, chlorobromuron, daimuron, methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, tri-allate, di-allate, esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxyidim, tralkoxydim, and clethodim;

U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5- triazin-zyl)-3-methylureidosulphonyl) benzoic acid esters such as the methyl ester thereof (DPX-LS300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glufosinate and its esters.

Y. organoarsenical herbicides such as monosodium methanearsonate (MSMA);

Z. herbicidal amide derivative such-as napropamide, propyzamide, carbetamide, tebutam, bromobutide, isoxaben, naproanilide and naptalam;

AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinclorac, dithiopyr triketone herbicides and mefanacet;

BB. Examples of useful contact herbicides include:
bipyridylium herbicides such as those in which the active entity is paraquat and those in which the active entity is diquat;
* These compounds are preferably employed in combination with a safener such as dichlormid.

The compositions of the present invention may be supplied in pre-mixed form or may be tank mixed shortly before application.

The invention is illustrated by the following Examples in which all parts and percentages are by weight unless otherwise indicated. Treatment rates (indicated for example as g/ha) are expressed in terms of the weight of active ingredient.

EXAMPLE 1

This Example illustrates the herbicidal activity and rainfastness of compositions of the present invention.

To an aqueous solution of the trimethylsulphonium salt of N-phosphonomethylglycine was added a pre-mixed adjuvant system containing equal parts by weight of an alkylpolyglucoside commercially available under the trademark AL2042 and a mixture of ethoxylated branched/linear $C_{13}$–$C_{15}$ alcohols having ethylene oxide contents of 11 and 20 respectively (SYNPERONIC A11 and SYNPERONIC A20 in the ratio of 60 to 40) giving an overall mean ethylene oxide content of about 15. It should be noted in this and subsequent Examples that ethoxylated alcohols supplied under the trade mark SYNPERONIC and used herein are all linear $C_{13}$–$C_{15}$ alcohols whose ethylene oxide content is indicated as the number after the suffix "A". The ratio of the trimethylsulphonium salt of N-phosphonomethylglycine to the adjuvant system was 2:1 by weight and the content of the trimethylsulphonium salt of N-phosphonomethylglycine in the concentrate was 271 g/kg. This composition is designated COMPOSITION 1 in Table 1 below.

A corresponding concentrate was prepared in which the adjuvant system contained AL2042, the mixture of SYNPERONIC A11 and A20 referred to above and a quaternary $C_{16}$ trimethyl ammonium chloride (ARQUAD 16–50— ARQUAD is a trademark of Akzo) in the proportions 1:1:1. The ratio of the trimethylsulphonium salt of N-phosphonomethylglycine to the adjuvant system was 2:1 by weight and the content of the trimethylsulphonium salt of N-phosphonomethylglycine in the concentrate was 330 g/kg. This composition is designated COMPOSITION 2 in Table 1 below.

The additional surfactant used in the concentrate (COMPOSITION 2) was found to provide excellent physical stability over a temperature range of –5° C. to 40° C.

The concentrates of the present invention were compared with a corresponding concentrate in which the adjuvant system contained AL2042 only. The ratio of the trimethylsulphonium salt of N-phosphonomethylglycine to the adjuvant system was 2:1 by weight and the content of the trimethylsulphonium salt of N-phosphonomethylglycine in the concentrate was 480 g/l. This composition is designated Comparison 1 in Table 1 below. A further comparison was undertaken with the commercially available glyphosate herbicide ROUNDUP (ROUNDUP is a trademark of Monsanto Co). This composition is designated Comparison 2 in Table 1 below.

Required aliquots of each formulation or adjuvant system were diluted to provide an application corresponding to 500 g glyphosate salt per ha applied at a spray volume rate equivalent to 200 l/ha. This was sprayed in three replicates onto young pot plants. Half the plants from each treatment were then returned to warm or temperate glasshouse environments as appropriate for optimal growth. The remaining plants were first subjected to simulated rain one hour after the treatments were applied by uniformly spraying with water at a rate of 4 mm in 30 seconds. The plants were then returned to the glasshouse.

Activity (damage to plants) was assessed 29 days after treatment by comparison with untreated plants on a 0–100% scale, where 0% is no damage and 100% is complete kill. The abbreviations used for the species treated in this and subsequent Examples is indicated in Table 2.

TABLE 1

ACTIVITY OF COMPOSITIONS WITH AND WITHOUT RAINWASH

| | Species | | | | | |
|---|---|---|---|---|---|---|
| | AGRRE | | SORHA | | CIRAR | |
| Composition | No Rainwash | Rain wash | No Rainwash | Rain wash | No Rainwash | Rain wash |
| Composition 1 | 83 | 40 | 100 | 93 | 72 | 35 |
| Composition 2 | 98 | 30 | 100 | 62 | 73 | 55 |
| Comparison 1 | 83 | 32 | 94 | 51 | 74 | 20 |
| Comparison 2 | 82 | 20 | 94 | 39 | 70 | 45 |

TABLE 2

| | |
|---|---|
| AGRRE | Elymus repens |
| SORHA | Sorghum halepense |
| CIRAR | Cirsium arvense |
| ELEIN | Eleusine indica |
| POANN | Poa annua |
| CYPRO | Cyperus rotundus |
| CHEAL | Chenopodium album |
| EPHHL | Euphorbia heterophylla |
| CONAR | Convolvulus arvensis |
| ERICA | Conyza canadersis |
| POLAV | Polygonum aviculare |
| SETVI | Setaria viridis |
| ABUTH | Abutilon theophrasti |

EXAMPLE 2

The procedure of Example 1 was repeated using an adjuvant system containing AL2042, and a mixture of SYNPERONIC A7 and SYNPERONIC A50. SYNPERONIC A7 has a mean ethylene oxide content of 7 and SYNPERONIC A50 has a mean ethylene oxide content of 50 and the two were mixed in the ratio 54:46. The ratio of AL2042 to the SYNPERONIC mixture was 1:1. The ratio of the trimethylsulphonium salt of N-phosphonomethylglycine to the adjuvant system was 2:1 by weight. This composition is designated COMPOSITION 1 in Table 3 below. COMPOSITION 1 was compared with the corresponding composition containing no ethoxylated alcohol component (COMPARISON 1).

The compositions were applied as in Example 1.

TABLE 3

ACTIVITY OF COMPOSITIONS WITH AND WITHOUT RAINWASH

| | Species | | | | | |
|---|---|---|---|---|---|---|
| | AGRRE | | SORHA | | CIRAR | |
| Composition | No Rainwash | Rain wash | No Rainwash | Rain wash | No Rainwash | Rain wash |
| Composition 1 | 87 | 25 | 96 | 83 | 75 | 22 |
| Comparison 1 | 83 | 32 | 94 | 51 | 74 | 20 |

EXAMPLE 3

The procedure of Example 1 was repeated using tank mixed compositions. Thus composition 1 contained the trimethylsulphonium salt of N-phosphonomethylglycine and an adjuvant system containing equal parts by weight of AL2042 and the mixture of SYNPERONIC A11 and A 20 referred to in Example 1. The ratio of the trimethylsulphonium salt of N-phosphonomethylglycine to the adjuvant system was 2:1 by weight. Composition 2 contained an adjuvant system having equal proportions of AL2042, the mixture of SYNPERONIC A11 and A20 and ARQUAD 16–50, the proportions of adjuvant system to the glyphosate salt being the same. A comparison was undertaken with the glyphosate salt containing the same proportion of an adjuvant system comprised only of AL2042.

All compositions were sprayed at a rate equivalent to 200 l/ha and 500 g glyphosate salt/ha. The procedure was the same as in Example 1 except that the damage was assessed at 23 days after treatment.

TABLE 4

| | Composition 1 | | Composition 2 | | Comparison 1 | |
|---|---|---|---|---|---|---|
| Species | No Rainwash | Rain wash | No Rainwash | Rain wash | No Rainwash | Rain wash |
| ELEIN | 90 | 80 | 95 | 76 | 89 | 50 |
| SORHA | 94 | 79 | 94 | 79 | 85 | 74 |
| AGRRE | 96 | 77 | 99 | 80 | 90 | 72 |
| POANN | 87 | 82 | 96 | 85 | 89 | 75 |
| CYPRO | 38 | 18 | 45 | 12 | 17 | 14 |
| CHEAL | 65 | 7 | 81 | 22 | 63 | 13 |
| EPHHL | 85 | 67 | 84 | 77 | 85 | 40 |
| CONAR | 30 | 17 | 23 | 7 | 13 | 4 |
| ERICA | 92 | 55 | 90 | 63 | 77 | 70 |
| POLAV | 74 | 71 | 87 | 68 | 78 | 31 |

EXAMPLE 4

The procedure of Example 3 was repeated exactly except that the proportion of AL2042 to the mixture of SYNPERONIC A11 and A20 referred to in Example 1 in the adjuvant system was varied from 1:1 (Composition 1) to 4:1 (Composition 2). The same comparison was used.

TABLE 5

| | Composition 1 | | Composition 2 | | Comparison 1 | |
|---|---|---|---|---|---|---|
| Species | No Rainwash | Rain wash | No Rainwash | Rain wash | No Rainwash | Rain wash |
| ELEIN | 90 | 80 | 89 | 83 | 89 | 50 |
| SORHA | 94 | 79 | 92 | 82 | 85 | 74 |
| AGRRE | 96 | 77 | 92 | 87 | 90 | 72 |
| POANN | 87 | 82 | 92 | 84 | 89 | 75 |
| CYPRO | 38 | 18 | 20 | 22 | 17 | 14 |
| CHEAL | 65 | 7 | 71 | 6 | 63 | 13 |
| EPHHL | 85 | 67 | 86 | 76 | 85 | 40 |
| CONAR | 30 | 17 | 17 | 5 | 13 | 4 |
| ERICA | 92 | 55 | 96 | 62 | 77 | 70 |
| POLAV | 74 | 71 | 78 | 69 | 78 | 31 |

EXAMPLE 5

This Example illustrates the synergistic effect of the adjuvant system of the present invention in respect of activity in the absence of rain. In each instance, the ajduvant system was added at a conentration of 0.25% w/v to a solution of the trimethylsulphonium salt of glyphosate.

The Compositions evaluated were:

Composition 1 trimethylsulphonium salt of glyphosate and an adjuvant system comprised of 1 part AL2042 and 1 part of a mixture of SYNPERONIC A11 and SYNPERONIC A20 mixed in the ratio of 60:40.

Composition 2 trimethylsulphonium salt of glyphosate and an adjuvant system comprised of 1 part AL2042 and 1 part of a mixture of RENEX 30 and SYNPERONIC A20 in the ratio 60:40.

Composition 3 trimethylsulphonium salt of glyphosate and an adjuvant system comprised of 7 parts AL2042 and 3 parts of a mixture of RENEX 30 and SYNPERONIC A20 in the ratio 60:40.

Comparison 1 trimethylsulphonium salt of glyphosate and an adjuvant system comprised only of AL2042.

Comparison 2 trimethylsulphonium salt of glyphosate and an adjuvant system comprised only of the mixture of SYNPERONIC ethoxylated alcohols referred to in Composition 1.

Comparison 3 trimethylsulphonium salt of glyphosate and an adjuvant system comprised only of the mixture of RENEX 30 and SYNPERONIC A20 in the ratio 60:40.

Required aliquots of each formulation or adjuvant system were diluted to provide an application corresponding to 125 g/ha of glyphosate salt for SETVI and SORHA and 250 g/ha of glyphosate salt for CHEAL and ABUTH. All compositions were applied at a spray volume rate equivalent to 200 l/ha. This was sprayed in three replicates onto young pot plants.

Activity (damage to plants) was assessed 7 and 14 days respectively after treatment by comparison with untreated plants on a 0–100% scale, where 0% is no damage and 100% is complete kill.

The results are shown in Table 6 for 7 days after treatment and Table 7 for 14 days after treatment.

TABLE 6

(7 DAYS AFTER TREATMENT)

| | SPECIES | | | |
|---|---|---|---|---|
| | SETVI | SORHA | CHEAL | ABUTH |
| Composition 1 | 78 | 60 | 59 | 46 |
| Composition 2 | 71 | 64 | 58 | 37 |
| Composition 3 | 59 | 69 | 63 | 44 |
| Comparison 1 | 57 | 6 | 46 | 24 |
| Comparison 2 | 61 | 1 | 42 | 36 |
| Comparison 3 | 47 | 0 | 26 | 33 |

TABLE 7

(14 days after treatment)

| | SPECIES | | | |
|---|---|---|---|---|
| | SETVI | SORHA | CHEAL | ABUTH |
| Composition 1 | 68 | 55 | 65 | 43 |
| Composition 2 | 66 | 62 | 72 | 42 |
| Composition 3 | 50 | 58 | 74 | 41 |
| Comparison 1 | 18 | 4 | 45 | 16 |
| Comparison 2 | 2 | 1 | 35 | 28 |
| Comparison 3 | 14 | 3 | 8 | 28 |

EXAMPLE 6

This Example illustrates the use in the present invention of a variety of ethoxylated alcohols. The results show that compositions of the present invention are in general at least as active in the absence of rain as corresponding composition without the ethoxylated alcohol and in most instances are actually more active. In each instance, the adjuvant system was added at a conentration of 0.25% w/v to a solution of the trimethylsulphonium salt of glyphosate.

Composition 1 trimethylsulphonium salt of glyphosate and an adjuvant system comprised of 1 part AL2042 and 1 part of a mixture of SYNPERONIC A11 and SYNPERONIC A20 mixed in the ratio of 60:40.

Composition 2 trimethylsulphonium salt of glyphosate and an adjuvant system comprised of 1 part AL2042 and 1 part of a mixture of SYNPERONIC A7 and SYNPERONIC A20 mixed in the ratio of 7:3.

Composition 3 trimethylsulphonium salt of glyphosate and an adjuvant system comprised of 1 part AL2042 and 1 part of a mixture of SYNPERONIC A2 and SYNPERONIC A20 mixed in the ratio of 12:88.

Composition 4 trimethylsulphonium salt of glyphosate and an adjuvant system comprised of 1 part AL2042 and 1 part of a mixture of SYNPERONIC A7 and SYNPERONIC A50 mixed in the ratio of 54:46.

Composition 5 trimethylsulphonium salt of glyphosate and an adjuvant system comprised of 1 part AL2042 and 1 part of a linear $C_{9-11}$ alcohol having an ethylene oxide content of 20.

Composition 6 trimethylsulphonium salt of glyphosate and an adjuvant system comprised of 1 part AL2042 and 1 part of SYNPERONIC A20.

Composition 7 trimethylsulphonium salt of glyphosate and an adjuvant system comprised of 1 part AL2042 and 1 part of a linear $C_{13}$ alcohol having an ethylene oxide content of 15.

Composition 8 trimethylsulphonium salt of glyphosate and an adjuvant system comprised of 1 part AL2042 and 1 part of a linear $C_{16-18}$ alcohol having an ethylene oxide content of 17.

The compositions were evaluated using the procedure of Example 5 at 14 days after treatment. The comparison formulation (Comparison 1) was the corresponding composition wherein the adjuvant system was comprised of AL2042 only. The results are presented in Table 8 below wherein the application rate for each species is indicated.

TABLE 8

(14 days after treatment)

| | SPECIES | | | | |
|---|---|---|---|---|---|
| | AGRRE 250 g/ha | CIRAR 125 g/ha | SORHA 250 g/ha | CHEAL 500 g/ha | ABUTH 500 g/ha |
| Composition 1 | 81 | 59 | 98 | 69 | 69 |
| Composition 2 | 76 | 63 | 85 | 68 | 60 |
| Composition 3 | 79 | 80 | 93 | 58 | 54 |
| Composition 4 | 70 | 73 | 53 | 67 | 47 |
| Composition 5 | 73 | 67 | 96 | 73 | 56 |
| Composition 6 | 82 | 61 | 93 | 68 | 62 |
| Composition 7 | 71 | 55 | 97 | 53 | 67 |
| Composition 8 | 81 | 66 | 96 | 82 | 88 |
| Comparison 1 | 72 | 61 | 78 | 63 | 48 |

EXAMPLE 7

This Example illustrates the further improvement in activity which may be obtained if a humectant is added to the composition of the present invention. In each instance, the adjuvant system was added at a conentration of 0.25% w/v to a solution of the trimethylsulphonium salt of glyphosate.

To a composition containing the trimethylsulphonium salt of glyphosate and an adjuvant system comprising a 1:1 mixture of AL2042 with a mixture of SYNPERONIC A11 and SYNPERONIC A20 in the ratio 60:40 was added humectant in the indicated proportion. The compositions were evaluated at 7 days after treatment using the method of Example 5 and the results are presented in Table 9.

TABLE 9

| | | SPECIES | | | |
|---|---|---|---|---|---|
| Humectant | Proportion % w/v | SETVI 125 g/ha | SORHA 250 g/ha | CHEAL 250 g/ha | ABUTH 500 g/ha |
| Glycerol | 1 | 67 | 71 | 45 | 73 |
| Glycerol | 5 | 83 | 66 | 61 | 60 |
| PEG 200* | 1 | 77 | 75 | 73 | 53 |
| PEG 200 | 5 | 78 | 78 | 63 | 77 |
| Sorbitol | 1 | 86 | 68 | 47 | 61 |
| Sorbitol | 5 | 93 | 69 | 49 | 42 |

TABLE 9-continued

| | | SPECIES | | | |
|---|---|---|---|---|---|
| Humectant | Proportion % w/v | SETVI 125 g/ha | SORHA 250 g/ha | CHEAL 250 g/ha | ABUTH 500 g/ha |
| Ethylene glycol | 1 | 58 | 45 | 39 | 63 |
| Ethylene glycol | 5 | 65 | 54 | 37 | 55 |
| Propylene glycol | 1 | 52 | 51 | 29 | 58 |
| Propylene glycol | 5 | 61 | 60 | 35 | 55 |
| Sodium lactate | 1 | 70 | 70 | 31 | 64 |
| Sodium lactate | 5 | 93 | 76 | 36 | 79 |
| PVA | 0.5 | 45 | 59 | 53 | 38 |
| None (control) | | 15 | 22 | 30 | 33 |

*Polyethylene glycol of molecular weight 200.

EXAMPLE 8

The stabilities of the following compositions of the present invention were evaluated:

Composition 10

| | |
|---|---|
| trimethylsulphonium salt of glyphosate | 320 g/l (based on salt) |
| Alylpolyglycoside (AL2042 - ICI) | 80 g/l |
| Ethoxylated alcohol* | 80 g/l |
| water | to 1 liter |

*A mixture of SYNPERONIC A11 and SYNPERONIC A20 mixed in the ratio of 60:40

Composition 11

| | |
|---|---|
| trimethylsulphonium salt of glyphosate | 320 g/l (based on salt) |
| Alkylpolyglycoside (AL2042 - ICI) | 80 g/l |
| Ethoxylated alcohol* | 80 g/l |
| ETHOQUAD C/12 (ETHOQUAD is a trademark of Akzo) | 53.3 g/l (40 g/l active surfactant) |
| water | to 1 liter |

*A mixture of SYNPERONIC A11 and SYNPERONIC A20 mixed in the ratio of 60:40

Composition 12

| | |
|---|---|
| trimethylsulphonium salt of glyphosate | 320 g/l (based on salt) |
| Alkylpolyglycoside (AL2042 - ICI) | 200 g/l |
| Ethoxylated alcohol* | 80 g/l |
| water | to 1 liter |

*A mixture of SYNPERONIC A11 and SYNPERONIC A20 mixed in the ratio of 60:40

Composition 13

| | |
|---|---|
| trimethylsulphonium salt of glyphosate | 320 g/l (based on salt) |
| Alkylpolyglycoside (AL2042 - ICI) | 80 g/l |
| Ethoxylated alcohol* | 80 g/l |
| ARQUAD 16-29 (ARQUAD is a trademark of Akzo) | 91.9 g/l (26.6 g/l active surfactant) |
| water | to 1 liter |

*A mixture of SYNPERONIC A11 AND SYNPERONIC A20 mixed in the ratio of 60:40

Composition 10 (with no additional surfactant) was a non-homogeneous solution at room temperature and separated into two layers. It is unsuitable as a commercial formulation. In an accelerated stability test, Compositions 11, 12 and 13 were homogeneous at room temperature and over the temperature range −5° C. to 40° C. when stored at these temperatures respectively over 1 week. Composition 13 was stored under ambient conditions for six months and showed no indication of phase separation.

Composition 12 remained homogeneous despite the absence of an additional surfactant but required a undesirably high proportion of the relatively expensive alkylpolyglycoside surfactant. Composition 11 was the most effective on a product basis.

EXAMPLE 9

The procedure of Example 1 was repeated using a composition (COMPOSITION 14) containing trimethylsulphonium salt of glyphosate (360 g/l based on salt); a mixture of SYNPERONIC A11 and SYNPERONIC A20 in the ratio 60:40 (60 g/l total); alkylpolyglycoside (AL2042- 60 g/l) and ARQUAD 16–50 (60 g/l based on the quaternary ammonium salt surfactant—ARQUAD 16–50 is a 50% solution of quaternary ammonium surfactant in isopropyl alcohol).

A corresponding composition (COMPOSITION 15) was prepared using ARQUAD 16–29 (60 g/l based on the ethoxylated quaternary ammonium salt surfactant—ARQUAD 16–29 is a 29% solution of surfactant in water)

Compositions 14 and 15 were compared with a composition containing 480 g/l trimethylsulphonium salt of glyphosate and 240 g/l AL2042 (COMPARISON).

The compositions were applied as in Example 1 and the activity (at 25 days after treatment) of the compositions with and without rainwashing (at one hour after spraying) is given in Table 10. The activity was calculated from a series of experiments using different concentrations and is presented in terms of the rate of active ingredient (g/ha trimethylsulphonium salt of glyphosate) required to give 90% control of the indicated weed species (ED90). Thus the lower the ED90 value in Table 10, the more active the composition.

TABLE 10

ACTIVITY (ED90) OF COMPOSITIONS WITH AND WITHOUT RAINWASH

| | Species | | | |
|---|---|---|---|---|
| | AGRRE | | SORHA | |
| Composition | No Rainwash | Rainwash | No Rainwash | Rainwash |
| Composition 14 | 447 | 2744 | 515 | 2687 |
| Composition 15 | 521 | 3658 | 520 | 3238 |
| COMPARISON | 1042 | >4000 | 849 | 4543 |

It will be seen that compositions of the present invention provide both improved activity in the absence of rain and improved rainfastness as compared with the comparison composition.

EXAMPLE 10

In this Example, the activities of compositions of the present invention were compared with standards in the absence of rain washing.

Adjuvant systems were prepared for tankmixing with the trimethylsulphonium salt of glyphosate as follows:

TABLE 11

| Adjuvant System | AL2042 (g/l) | Ethoxylated alcohol* (total g/l) | ARQUAD 16–50 (g/l as active surfactant) |
|---|---|---|---|
| System 1 | 80 | 80 | 80 |
| System 2 | 160 | 80 | 0 |
| System 3 | 110 | 50 | 80 |
| System 4 | 160 | 40 | 40 |
| COMPARISON | 240 | 0 | 0 |

*a mixture of SYNPERONIC A11 and SYNPERONIC A20 in the ratio 60:40

It will be seen that in each instance the total adjuvant content represents 240 g/l.

Each adjuvant system was added in a tank mix at 0.125, 0.25, 0.5 and 1.0% (w/v) respectively based on total adjuvant to 125, 250, 500, and 1000 g/ha trimethylsulphonium salt of glyphosate respectively in 200 l/ha water and the resultant diluted composition was sprayed on the target species. The activity at 14 days after treatment was determined as in Example 9 by calculating the rate (g/l) of trimethylsulphonium salt of glyphosate required to achieve 90% control of the target species. The results are presented in Table 12 for the species SORHA and Table 13 for the species AGRRE.

TABLE 12

ED 90 (SORHA)

| Adjuvant System | Adjuvant content (% w/v) | | | |
|---|---|---|---|---|
|  | 0.125 | 0.25 | 0.5 | 1.0 |
| 1 | 615 | 456 | 442 | 379 |
| 2 | 814 | 570 | 332 | 244 |
| 3 | 557 | 367 | 366 | 400 |
| 4 | 768 | 673 | 362 | 377 |
| COMPARISON | 867 | 640 | 464 | 401 |

TABLE 13

ED90 (AGRRE)

| Adjuvant System | Adjuvant content (% w/v) | | | |
|---|---|---|---|---|
|  | 0.125 | 0.25 | 0.5 | 1.0 |
| 1 | 761 | 674 | 532 | 388 |
| 2 | 1452 | 919 | 624 | 453 |
| 3 | 798 | 704 | 428 | 409 |
| 4 | 965 | 1149 | 617 | 774 |
| COMPARISON | 965 | 908 | 662 | 1254 |

The results show that at preferred proportions of components, the composition comprising the quaternary ammonium surfactant in addition to the alkylpolyglycoside and the ethoxylated alcohol shows significantly increased activity.

EXAMPLE 11

Adjuvant systems were prepared for tank-mixing with the trimethylsulphonium salt of glyphosate to provide compositions whose components were sprayed at the following rates:

Composition 16:

| Trimethylsulphonium salt of glyphosate | 500 g/ha |
|---|---|
| AL2042 | 83 g/ha |
| Ethoxylated alcohol* | 83 g/ha |
| ARQUAD 16–19 | 83 g/ha (based on active surfactant) |

Composition 17

| Trimethylsulphonium salt of glyphosate | 500 g/ha |
|---|---|
| AL2042 | 125 g/ha |
| Ethoxylated alcohol* | 125 g/ha |
| COMPARISON |  |
| Trimethylsulphonium salt of glyphosate | 500 g/ha |
| AL2042 | 250 g/ha |

*a mixture of SYNPERONIC A11 and SYNPERONIC A20 in the ratio 60:40

Activity (damage to plants) was assessed according to the procedure of Example 1 at 25 days after treatment by comparison with untreated plants on a 0–100% scale, where 0% is no damage and 100% is complete kill. All results were a mean of three replicates. The activity in the absence of rain was compared with that obtained when a rainwash was applied at 1 hour after treatment. The results are presented in Table 14.

TABLE 14

|  | Species | | | |
|---|---|---|---|---|
|  | AGRRE | | SORHA | |
| Composition | No Rainwash | Rainwash | No Rainwash | Rainwash |
| Composition 16 | 97 | 64 | 98 | 57 |
| Composition 17 | 95 | 53 | 96 | 62 |
| COMPARISON | 91 | 33 | 93 | 42 |

EXAMPLE 12

Adjuvant systems were prepared for tank-mixing with the trimethylsulphonium salt of glyphosate to provide compositions whose components were sprayed at the following rates:

Composition 18

| Trimethylsulphonium salt of glyphosate | 500 g/ha |
|---|---|
| AL2042 | 125 g/ha |
| Ethoxlated alcohol* | 125 g/ha |

Composition 19

| Trimethylsulphonium salt of glyphosate | 500 g/ha |
|---|---|
| AL2042 | 125 g/ha |
| Ethoxylated alcohol* | 125 g/ha |
| ARQUAD 16–19 | 41.5 g/ha (based on active surfactant) |

Composition 20

| Trimethylsulphonium salt of glyphosate | 500 g/ha |
|---|---|
| AL2042 | 125 g/ha |

| | |
|---|---|
| Ethoxylated alcohol* | 125 g/ha |
| ETHOQUAD C/12 | 41.5 g/ha (based on active surfactant) |

COMPARISON

| | |
|---|---|
| Trimethylsulphonium salt of glyphosate | 500 g/ha |
| AL2042 | 250 g/ha |

*a mixture of SYNPERONIC A11 and SYNPERONIC A20 in the ratio 60:40

Activity (damage to plants) was assessed according to the procedure of Example 1 at 25 days after treatment by comparison with untreated plants on a 0–100% scale, where 0% is no damage and 100% is complete kill. All results were a mean of three replicates. The activity in the absence of rain was compared with that obtained when a rainwash was applied at 3 hours after treatment. The results are presented in Table 15.

TABLE 15

| | Species | | | |
|---|---|---|---|---|
| | AGRRE | | SORHA | |
| Composition | No Rainwash | Rainwash | No Rainwash | Rainwash |
| Composition 18 | 98 | 88 | 99 | 93 |
| Composition 19 | 98 | 87 | 98 | 95 |
| Composition 20 | 98 | 94 | 98 | 85 |
| COMPARISON | 98 | 81 | 94 | 68 |

EXAMPLE 13

Adjuvant systems were prepared for tank-mixing with the trimethylsulphonium salt of glyphosate to provide compositions whose components were sprayed at the following rates:

Composition 21

| | |
|---|---|
| Trimethylsulphonium salt of glyphosate | 500 g/ha |
| AL2042 | 83.3 g/ha |
| Ethoxylated alcohol* | 83.3 g/ha |
| ARQUAD 16–19 | 53.3 g/ha (based on active surfactant) |

Composition 22

| | |
|---|---|
| Trimethylsulphonium salt of glyphosate | 500 g/ha |
| AL2042 | 83.3 g/ha |
| Ethoxylated alcohol* | 83.3 g/ha |
| ARQUAD C/12 | 53.3 g/ha (based on active surfactant) |

COMPARISON 1

| | |
|---|---|
| Trimethylsulphonium salt of glyphosate | 560 g/ha |
| AL2042 | 83.3 g/ha |
| Ethoxylated alcohol* | 83.3 g/ha |
| ETHOQUAD 16–29 | 83.3 g/ha (based on active surfactant) |

COMPARISON 2

| | |
|---|---|
| Trimethylsulphonium salt of glyphosate | 500 g/ha |
| AL2042 | 250 g/ha |

*a mixture of SYNPERONIC A11 and SYNPERONIC A20 in the ratio 60:40

Activity.(damage to plants) was assessed according to the procedure of Example 1 at 25 days after treatment by comparison with untreated plants on a 0–100% scale, where 0% is no damage and 100% is complete kill. All results were a mean of three replicates. The activity in the absence of rain was compared with that obtained when a rainwash was applied at 3 hours after treatment. The results are presented in Table 16.

TABLE 16

| | Species | | | |
|---|---|---|---|---|
| | AGRRE | | SORHA | |
| Composition | No Rainwash | Rainwash | No Rainwash | Rainwash |
| Composition 21 | 98 | 93 | 99 | 97 |
| Composition 22 | 98 | 94 | 99 | 83 |
| COMPARISON 1 | 98 | 81 | 97 | 84 |
| COMPARISON 2 | 98 | 81 | 94 | 68 |

We claim:

1. A glyphosate composition having improved rainfastness comprising (i) N-phosphonomethylglycine or an agriculturally acceptable salt thereof, (ii) an alkylpolyglycoside surfactant and (iii) an ethoxylated alcohol wherein the ethoxylated alcohol is obtained by ethoxylation of a linear or branched chain aliphatic mono alcohol having a chain length of from 8 to 20 carbon atoms and has a mean degree of ethoxylation of from 2 to 50 moles of ethylene oxide per mole of alcohol.

2. A composition according to claim 1 wherein the alkylpolyglycoside is obtained by the reaction of glucose with a straight or branched chain alkanol or mixture of alkanols having an average of from 7 to 18 carbon atoms and an average number of glycose groups per alkyl group of between 1 and 4.

3. A composition according to claim 1 or wherein the ethoxylated alcohol is obtained by ethoxylation of a linear or branched chain aliphatic mono alcohol having a chain length of from 10 to 18 carbon atoms and has a mean degree of ethoxylation of from 11 to 18 moles of ethylene oxide per mole of alcohol.

4. A composition according to claim 1 wherein the proportion of alkylpolyglycoside is from 1 part by weight of alkylpolyglycoside per 5 parts by weight of ethoxylated alcohol to 8 parts by weight of alkylpolyglycoside per 1 part by weight of ethoxylated alcohol.

5. A composition according to claim 4 wherein the proportion of alkylpolyglycoside is from 0.5 parts by weight of alkylpolyglycoside per 1 part by weight of ethoxylated alcohol to 8 parts by weight of alkylpolyglycoside per 1 part by weight of ethoxylated alcohol.

6. A composition according to claim 1 which contains an additional surfactant which is a cationic or non-ionic surfactant containing an amine, ammonium or amine oxide group.

7. A composition according to claim 6 wherein the additional surfactant is an optionally ethoxylated quaternary ammonium salt having at least one long chain substituent containing from 10 to 20 carbon atoms and a mean ethylene oxide content of from 0 to 5.

8. A composition according to claim 6 wherein the proportion of the additional surfactant is from 0 to 2 parts by weight per 1 part by weight of ethoxylated alcohol.

9. A composition according to claim 6 wherein the total adjuvant system comprises substantially equal proportions by weight of alkylpolyglycoside, ethoxylated alcohol and additional surfactant.

10. A composition according to claim 6 which is a herbicidal concentrate wherein there is used a water-soluble salt of N-phosphonomethylglycine and the concentration of the N-phosphonomethylglycine salt is greater than 210 g/l based on glyphosate acid.

11. A composition according to claim 1 wherein the proportion by weight of the total adjuvant system, being the alkylpolyglycoside, ethoxylated alcohol and additional surfactant if used, to the N-phosphonomethylglycine or the agriculturally acceptable salt thereof is from 3:1 to 1:3.

12. A composition according to claim 1 which additionally comprises a humectant.

13. A process of severely damaging or killing unwanted plants, and more particularly a process of providing enhanced activity or enhanced rainfastness which comprises applying to the plants a herbicidally effective amount of a composition according to claim 1.

14. An adjuvant composition suitable for admixture with N-phosphonomethylglycine or an agriculturally acceptable salt thereof to form a composition according to claim 1, which adjuvant composition comprises (i) a alkylpolyglycoside surfactant and (ii) an ethoxylated alcohol wherein the ethoxylated alcohol is obtained by ethoxylation of a linear or branched chain aliphatic mono alcohol having a chain length of from 8 to 20 carbon atoms and has a mean degree of ethoxylation of from 2 to 50 moles of ethylene oxide per mole of alcohol and optionally (iii) an additional surfactant.

* * * * *